(12) United States Patent
Lewis (10) Patent No.: US 10,150,784 B2
(45) Date of Patent: Dec. 11, 2018

(54) CRYSTAL POLYMORPH OF MAGNESIUM GLYCINATE DIHYDRATE AND PROCESS FOR ITS PREPARATION

(71) Applicant: Cypress Pharmaceuticals, Inc., Morristown, NJ (US)

(72) Inventor: Robert L. Lewis, Madison, MS (US)

(73) Assignee: Cypress Pharmaceuticals, Inc., Morristown, NJ (US)

( * ) Notice: Subject to any disclaimer, the term of this patent is extended or adjusted under 35 U.S.C. 154(b) by 0 days.

(21) Appl. No.: 15/212,460

(22) Filed: Jul. 18, 2016

(65) Prior Publication Data

US 2016/0326188 A1 Nov. 10, 2016

Related U.S. Application Data (62) Division of application No. 14/091,070, filed on Nov. 26, 2013, now Pat. No. 9,394,318.

(60) Provisional application No. 61/731,885, filed on Nov. 30, 2012.

(51) Int. Cl.
*C07F 3/02* (2006.01)
*C07F 3/00* (2006.01)
*A61K 31/198* (2006.01)

(52) U.S. Cl.
CPC .............. *C07F 3/02* (2013.01); *A61K 31/198* (2013.01); *C07F 3/003* (2013.01)

(58) Field of Classification Search
None
See application file for complete search history.

(56) References Cited

U.S. PATENT DOCUMENTS

| | | |
|---|---|---|
| 8,236,358 B1 | 8/2012 | Lewis et al. |
| 8,247,000 B2 | 8/2012 | Lewis |
| 9,394,318 B2 * | 7/2016 | Lewis ................. C07F 3/02 |
| 2003/0147995 A1 | 8/2003 | Koss et al. |
| 2003/0206969 A1 | 11/2003 | Nidamarty et al. |
| 2005/0214383 A1 | 9/2005 | Bubnis et al. |
| 2007/0014876 A1 | 1/2007 | Shapira et al. |
| 2008/0318924 A1 | 12/2008 | Matsushima et al. |
| 2009/0269399 A1 | 10/2009 | Lewis et al. |

FOREIGN PATENT DOCUMENTS

| | | |
|---|---|---|
| DE | 29910454 U1 | 9/1999 |
| JP | 2008069173 A | 3/2008 |
| WO | 99/15189 A1 | 4/1999 |
| WO | 2007056405 A2 | 5/2007 |
| WO | 2008116215 A2 | 9/2008 |
| WO | 2008116226 A2 | 9/2008 |

OTHER PUBLICATIONS

All Chemicals: Magnesium Glycinate, Dihydrate, 11.7% Powder [online]. AllChemicals, 2007 [retrieved on May 12, 2015]. Retrieved from the internet: <http://www.labdepotinc.com/p-19215-magnesium-glycinate-dihydrate-117-powderphp?c=498>.
PCT International Search Report and Written Opinion in PCT/US09/40213 dated Dec. 21, 2009, 11 pages.
USPTO STIC-1600/2900 email, Search for publication date for AllChemicals Website showing Magnesium Glycinate Dihydrate mailed Feb. 18, 2016.
Bleyer, A.J., et al., "A Comparison of the Calcium-Free Phosphate Binder Sevelamer Hydrochloride with Calcium Acetate in the Treatment of Hyperphosphatemia in Hemodialysis Patients", Am. J. Kidney Dis., vol. 33, No. 4, pp. 694-701, 1999.
Deuber, H.J., "Combined Use of Calcium Acetate and Magnesium Carbonate as Phosphate Binder", vol. 33, No. 8, pp. 403-408, 2004.
Guillot, Ann P., et al., "The Use of Magnesium-Containing Phosphate Binders in Patients with End-Stage Renal Disease on Maintenance Hemodialysis", Nephron, vol. 30, No. 2, pp. 114-117 (1982).
Joy, Melanie S., et al., "Randomized, Double-Blind, Placebo-Controlled, Dose-Titration, Phase III Study Assessing the Efficacy and Tolerability of Lanthanum Carbonate: A New Phosphate Binder for the Treatment of Hyperphosphatemia", Am. J. Kidney Dis., vol. 42, No. 1, pp. 96-107 (2003).
Lowry, Oliver H., et al., "The Determination of Inorganic Phosphate in the Presence of Labile Phosphate Esters", J. Biol. Chem. 162, pp. 421-428 (1946).
Rosenbaum, D.P., et al., "Effect of RenaGel, a non-absorbable, cross-linked, polymeric phosphate binder, on urinary phosphorus excretion in rats", Nephrol Dial Transplant 12, pp. 961-964 (1997).
Sheldrick, George M., "A Short History of Shelx", Acta Cryst., A64, pp. 112-122 (2008).

* cited by examiner

*Primary Examiner* — Katherine Pebbles
(74) *Attorney, Agent, or Firm* — Servilla Whitney LLC (57) ABSTRACT

Embodiments of the invention provide solid forms of magnesium glycinate dihydrate and compositions thereof, which are useful for treating hyperphosphatemia and which exhibit desirable characteristics for the same. The invention further provides processes for the production of solid forms of magnesium glycinate dihydrate.

5 Claims, 4 Drawing Sheets

CRYSTAL POLYMORPH OF MAGNESIUM GLYCINATE DIHYDRATE AND PROCESS FOR ITS PREPARATION

CROSS-REFERENCE TO RELATED APPLICATION

This application is a divisional of U.S. application Ser. No. 14/091,070, filed Nov. 26, 2013, which claims the benefit under 35 USC § 119(e) of U.S. Provisional Application No. 61/731,885, filed Nov. 30, 2012, which are incorporated herein by reference in their entirety

FIELD OF THE INVENTION

The present invention provides solid forms of a compound of magnesium glycinate dihydrate, which may be characterized by increased phosphate binding capacity. The invention also provides pharmaceutically acceptable compositions comprising solid forms of the present invention and methods of using the compositions in the treatment of various disorders. The invention also provides methods of producing the novel solid forms disclosed herein.

BACKGROUND OF THE INVENTION

Like other diseases for which there is no cure, chronic kidney disease takes an ever-increasing toll on patients who have it. As the disease progresses, the kidney becomes less efficient at removing various ions from the blood. Among these ions is phosphate, which can form insoluble particles when combined with calcium. In end-stage renal disease, the final stage of chronic kidney disease, kidney function is so compromised that phosphate levels in the blood (serum) become markedly elevated. This condition, known as hyperphosphatemia, carries with it many grave health risks. For example, when serum phosphate and calcium levels are above a certain threshold, hardened deposits may form throughout the body, endangering circulation. It is therefore very important to control serum phosphate levels in patients with end-stage renal disease.

Patients with end-stage renal disease may be advised to eat a diet low in phosphate. However, phosphate is present at some level in almost all the foods we eat. For this reason, phosphate binders were developed. Phosphate binders are compounds taken orally and which act in the gastrointestinal tract to bind phosphate and keep it from being absorbed. Phosphate binders are generally taken with each meal. Phosphate binders known in the art include, for example, various salts of aluminum and calcium, as well as some chemically synthesized crosslinked polymers. There are clinical circumstances in which the administration of aluminum or calcium salts is ill-advised. In animal models, certain crosslinked polymers carry with them elevated risks of carcinogenesis. Therefore, there is a need for safer and more effective phosphate binders.

SUMMARY OF THE INVENTION

It has now been found that the novel solid forms of the present invention generated by the processes disclosed herein, and compositions thereof, are useful for the treatment of hyperphosphatemia and exhibit desirable characteristics for the same. In general, these solid forms, and pharmaceutically acceptable compositions thereof, are useful for treating or lessening the severity of a variety of diseases or disorders as described in detail herein.

Embodiments of the invention comprise a crystalline dihydrate form of magnesium glycinate (formula I)

Formula I

In some embodiments, the form is characterized by an X-ray powder diffraction pattern having one or more peaks selected from those at about 14.6, 16.0, 16.9, 17.6, 19.3, 22.9, 24.4, 25.8, 30.9 or 47.1. In some embodiments the form is characterized by an X-ray powder diffraction pattern having two or more peaks selected from those at about 14.6, 16.0, 16.9, 17.6, 19.3, 22.9, 24.4, 25.8, 30.9 or 47.1. In some embodiments, the form is characterized by an X-ray powder diffraction pattern having three or more peaks selected from those at about 14.6, 16.0, 16.9, 17.6, 19.3, 22.9, 24.4, 25.8, 30.9 or 47.1. In some embodiments, the form has substantially all of the peaks in its X-ray powder diffraction pattern selected from those at about 14.6, 16.0, 16.9, 17.6, 19.3, 22.9, 24.4, 25.8, 30.9 or 47.1. In some embodiments, the form has substantially all of the peaks in its X-ray powder diffraction pattern selected from those at about:

| No. | 2-Theta ° | Δ 2θ (±)° | d, Å |
|-----|-----------|-----------|------|
| 1   | 14.6      | 0.1       | 6.06 |
| 2   | 16.0      | 0.1       | 5.54 |
| 3   | 16.9      | 0.1       | 5.25 |
| 4   | 17.6      | 0.1       | 5.04 |
| 5   | 19.3      | 0.1       | 4.59 |
| 6   | 22.9      | 0.1       | 3.88 |
| 7   | 24.4      | 0.1       | 3.65 |
| 8   | 25.8      | 0.1       | 3.46 |
| 9   | 30.9      | 0.1       | 2.89 |
| 10  | 47.1      | 0.1       | 1.93 |

In some embodiments, the crystalline magnesium glycinate dihydrate has a space group P21/n. In some embodiments, the crystalline magnesium glycinate dihydrate has unit cell dimensions of about a=7.5 Å, b=9.0 Å, and c=13.0 Å. In some embodiments, the crystalline magnesium glycinate dihydrate has unit cell dimensions of about a=7.548 Å, b=9.053 Å, and c=12.970 Å. In some embodiments, the crystalline magnesium glycinate dihydrate has unit cell dimensions of about a=7.575 Å, b=9.153 Å, and c=13.052 Å.

In some embodiments, a crystalline magnesium glycinate dihydrate form is characterized by one or more of the following structural parameters:

| | | |
|---|---|---|
| Empirical formula | $C_4 H_{12} Mg N_2 O_6$ | |
| Formula weight | 208.47 | |
| Temperature | 147(2) K | |
| Wavelength | 1.54178 Å | |
| Crystal system | Monoclinic | |
| Space group | P 21/n | |
| Unit cell dimensions | a = 7.5481(3) Å | α = 90° |
| | b = 9.0525(3) Å | β = 98.612(3)° |
| | c = 12.9702(5) Å | γ = 90° |
| Volume | 876.25(6) Å³ | |
| Z | 4 | |

| | |
|---|---|
| Density (calculated) | 1.580 Mg/m³ |
| Absorption coefficient | 1.893 mm⁻¹ |
| F(000) | 440 |
| Crystal size | 0.10 × 0.01 × 0.01 mm³ |
| Theta range for data collection | 5.98 to 66.64° |
| Index ranges | −8 <= h <= 7, −10 <= k <= 10, −10 <= l <= 15 |
| Reflections collected | 5746 |
| Independent reflections | 1501 [R(int) = 0.0279] |
| Completeness to theta = 66.64° | 97.2% |
| Absorption correction | Semi-empirical from equivalents |
| Max. and min. transmission | 0.7528 and 0.6842 |
| Refinement method | Full-matrix least-squares on F² |
| Data/restraints/parameters | 1501/0/150 |
| Goodness-of-fit on F² | 1.056 |
| Final R indices [I > 2sigma(I)] | R1 = 0.0269, wR2 = 0.0696 |
| R indices (all data) | R1 = 0.0303, wR2 = 0.0718 |
| Largest diff. peak and hole | 0.215 and −0.224 e · Å⁻³ |

In another aspect of the invention, there is provided a pharmaceutical composition comprising crystalline form(s) of magnesium glycinate dihydrate as described herein. Some embodiments of the pharmaceutical composition comprise an enteric coating. In some embodiments, the enteric coating comprises acetyltributyl citrate, carbomers, cellulose acetate phthalate, cellulose acetate succinate, ethyl cellulose, guar gum, hypromellose acetate succinate, hypromellose phthalate, polymethacrylates, polyvinyl acetate phthalate, shellac, tributyl citrate, triethyl citrate, white wax and/or zein. In certain embodiments, the enteric coating that is stable at pH less than 3 but dissolves at a pH above 5.5. In some embodiments, the pharmaceutical composition further comprises one or more additional therapeutic agents or nutrients. Nutrients may be selected from vitamins, minerals, fatty acids, and/or amino acids.

Another aspect of the invention provides methods of treating hyperphosphatemia in a subject comprising administering to the subject a form of the magnesium glycinate dihydrate disclosed herein. In some embodiments, the form is a component of the pharmaceutical compositions disclosed herein.

In another aspect of the invention, there is provided processes of manufacturing magnesium glycinate dihydrate comprising dissolving magnesium methoxide and glycine in methanol. Some embodiments further comprise heating the solution. Some embodiments further comprise adding a volume of water to the mixture. Some embodiments further comprise heating the solution a second time. Some embodiments further comprise precipitating magnesium glycinate dihydrate from the mixture. In particular embodiments, the mixture of magnesium methoxide and glycine is heated at approximately 50-55° C. for at least 30 minutes. In certain embodiments, precipitating magnesium glycinate dihydrate comprises cooling to less than 25° C. for at least 30 minutes.

In another aspect of the invention, there is provided a crystalline polymorph of magnesium glycinate dihydrate made by the processes described herein.

DETAILED DESCRIPTION OF THE INVENTION

General Description of Certain Aspects of the Invention:

U.S. application Ser. No. 12/422,012 ("the '012 application"), now U.S. Pat. No. 8,247,000, filed Apr. 10, 2009, the entirety of which is hereby incorporated herein by reference, describes compositions of magnesium glycinate salt characterized by an ability to bind at least 50 mg phosphate per gram in an in vitro phosphate binding assay, which are suitable for treatment of hyperphosphatemia. Such compounds, which may be represented by the structure below, include formulations for oral administrations and enteric coatings:

(Structure 1)

Related U.S. Pat. No. 8,236,358, also incorporated by reference herein, describes methods of treating hyperphosphatemia with magnesium glycinate compositions.

Different preparations and forms of magnesium glycinate may be characterized by different phosphate binding capacities. In other words, particular solid forms of magnesium glycinate can be characterized by their phosphate-binding capacity as determined by various phosphate-binding assays known in the art. In some embodiments, solid forms of magnesium glycinate dihydrate can be characterized by their phosphate binding capacity under conditions that simulate small intestinal fluid (SIF), where said forms exhibit therapeutic action in mammalian subjects. Exemplary phosphate-binding assays in solutions simulating SIF are described in the '012 application. Additional phosphate-binding assays are described in Rosenbaum et al. Nephrol. Dial. Transplant. 12:961-964 (1997); and Lowry & Lopez J. Biol. Chem. 162:421-428 (1946), the teachings of which are incorporated by reference herein.

It would be desirable to provide a solid form of magnesium glycinate that, as compared to known forms, imparts characteristics such as improved aqueous solubility, stability, ease of formulation and is morphologically pure. Accordingly, the present invention provides novel solid forms of magnesium glycinate. Furthermore, embodiments of the invention comprise novel methods for production of said solid forms. Additional embodiments of the invention provide methods of treating hyperphosphatemia using the novel solid forms of magnesium glycinate.

Accordingly, embodiments of the invention provide solid crystalline forms of magnesium glycinate. Exemplary solid forms are described in more detail below, including particular embodiments of magnesium glycinate dihydrate.

In some embodiments, the present invention provides magnesium glycinate forms substantially free of impurities. As used herein, the term "substantially free of impurities" means that the compound contains no significant amount of extraneous matter. Such extraneous matter may include starting materials, residual solvents, or any other impurities that may result from the preparation of, and/or isolation of, magnesium glycinate. In preferred embodiments, the magnesium glycinate forms are substantially free of magnesium hydroxide. In certain embodiments, at least about 95% by weight of magnesium glycinate is present. In still other embodiments of the invention, at least about 99% by weight of magnesium glycinate is present.

According to one embodiment, a novel magnesium glycinate form is present in an amount of at least about 95, 97, 97.5, 98.0, 98.5, 99, 99.5, or 99.8 weight percent where the percentages are based on the total weight of the composition. According to another embodiment, a novel magnesium glycinate form contains no more than about 3.0 area percent HPLC of total organic impurities and, in certain embodiments, no more than about 1.5 area percent HPLC total organic impurities relative to the total area of the HPLC chromatogram. In other embodiments, a novel magnesium glycinate form contains no more than about 1.0 area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The novel magnesium glycinate forms also include all tautomeric forms. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

Embodiments of the present invention include pharmaceutical compositions comprising magnesium glycinate dihydrate in substantially polymorph form described by one or more x-ray powder diffraction peaks described below and exemplified in FIG. 1. The pharmaceutical compositions may be administered to a subject in need thereof in any dosage form; for example, those described in the '012 application.

According to another aspect of the invention, a process for the preparation of magnesium glycinate dihydrate is provided. In certain embodiments, the process results in magnesium glycinate dihydrate in substantially polymorph form described by one or more x-ray powder diffraction peaks described below and exemplified in FIG. 1.

Solid Forms of Magnesium Glycinate:

It has been found that magnesium glycinate can exist in a variety of solid forms. Such forms may be amorphous. Moreover, magnesium glycinate can exist in a variety of crystalline forms, called polymorphs. The solid forms can be solvates, hydrates and unsolvated forms of magnesium. All such forms are contemplated by the present invention. In certain embodiments, the present invention provides magnesium glycinate as a mixture of one or more solid forms of magnesium glycinate. In a particular embodiment, the present invention provides magnesium glycinate as a dihydrated polymorph.

As used herein, the term "polymorph" refers to the different crystal structures (of solvated or unsolvated forms) in which a compound can crystallize.

As used herein, the term "solvate" refers to a solid form with either a stoichiometric or non-stoichiometric amount of solvent (e.g., a channel solvate). For polymorphs, the solvent is incorporated into the crystal structure. Similarly, the term "hydrate" refers to a solid form with either a stoichiometric or non-stoichiometric amount of water. For polymorphs, the water is incorporated into the crystal structure.

As used herein, the term "about", when used in reference to a degree 2-theta value refers to the stated value ±0.3 degree 2-theta. In certain embodiments, "about" refers to +0.2 degree 2-theta or ±0.1 degree 2-theta.

In certain embodiments, magnesium glycinate dihydrate is a crystalline solid. In some embodiments, magnesium glycinate dihydrate is a crystalline solid substantially free of amorphous magnesium glycinate. As used herein, the term "substantially free of amorphous magnesium glycinate" means that the compound contains no significant amount of amorphous magnesium glycinate. In certain embodiments, at least about 95% by weight of crystalline magnesium glycinate dihydrate is present. In still other embodiments of the invention, at least about 97%, 98% or 99% by weight of crystalline magnesium glycinate dihydrate is present.

In certain embodiments, the present invention provides a crystal form of magnesium glycinate dihydrate. According to one embodiment, the form is characterized in that it has one or more peaks in its powder X-ray diffraction pattern selected from those at about 14.6, 16.0, 16.9, 17.6, 19.3, 22.9, 24.4, 25.8, 30.9 or 47.1 degrees 2-theta. In some embodiments, the form is characterized in that it has two or more peaks in its powder X-ray diffraction pattern selected from those at about 14.6, 16.0, 16.9, 17.6, 19.3, 22.9, 24.4, 25.8, 30.9 or 47.1 degrees 2-theta. In certain embodiments, the form is characterized in that it has three or more peaks in its powder X-ray diffraction pattern selected from those at about 14.6, 16.0, 16.9, 17.6, 19.3, 22.9, 24.4, 25.8, 30.9 or 47.1 degrees 2-theta. In particular embodiments, the form is characterized in having substantially all of the peaks in its X-ray powder diffraction pattern selected from those at about 14.6, 16.0, 16.9, 17.6, 19.3, 22.9, 24.4, 25.8, 30.9 or 47.1 degrees 2-theta. In an exemplary embodiment, the form is characterized in having substantially all of the peaks in its X-ray powder diffraction pattern selected from those at about:

TABLE 1

| No. | 2-Theta ° | Δ 2θ (±)° | d, Å |
|---|---|---|---|
| 1 | 14.6 | 0.1 | 6.06 |
| 2 | 16.0 | 0.1 | 5.54 |
| 3 | 16.9 | 0.1 | 5.25 |
| 4 | 17.6 | 0.1 | 5.04 |
| 5 | 19.3 | 0.1 | 4.59 |
| 6 | 22.9 | 0.1 | 3.88 |
| 7 | 24.4 | 0.1 | 3.65 |
| 8 | 25.8 | 0.1 | 3.46 |
| 9 | 30.9 | 0.1 | 2.89 |
| 10 | 47.1 | 0.1 | 1.93 |

Figure 1:
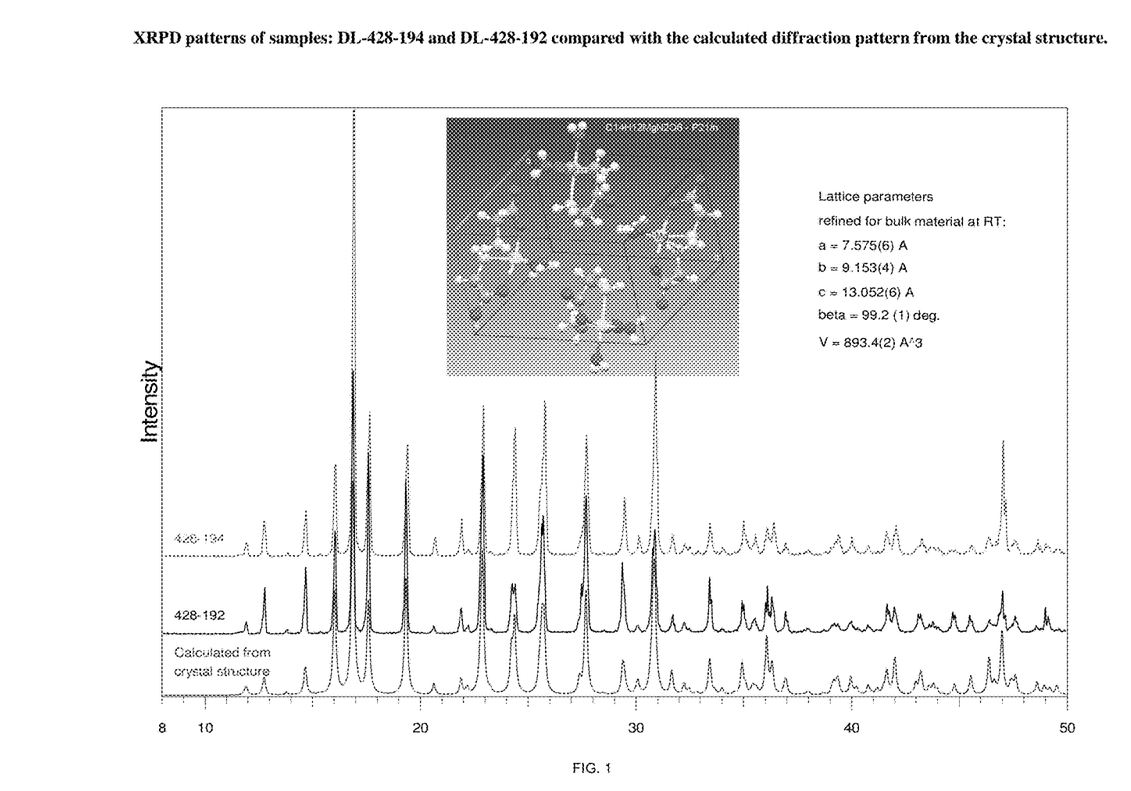
FIG. 1 depicts the x-ray powder diffraction (XRPD) pattern for two samples of a compound and of the invention and compares those patterns to a spectra calculated from a single crystal-derived x-ray structure of the compound.

According to one aspect, the form has a powder X-ray diffraction pattern substantially similar or essentially identical to that depicted in FIG. 1. According to another aspect, the form has a crystal lattice structure substantially similar to that depicted in FIG. 2. Accordingly to yet another aspect, the form is a single dihydrated complex substantially similar to that depicted in FIG. 3. The form can be characterized by substantial similarity to two or more of these figures simultaneously.

According to another embodiment of the invention, there is provided a crystalline polymorph of magnesium glycinate dihydrate that is characterized by one or more of the crystal structure parameters as set forth in Table 2 below:

TABLE 2

| | |
|---|---|
| Empirical formula | $C_4 H_{12} Mg N_2 O_6$ |
| Formula weight | 208.47 |
| Temperature | 147(2) K |
| Wavelength | 1.54178 Å |
| Crystal system | Monoclinic |
| Space group | P 21/n |
| Unit cell dimensions | a = 7.5481(3) Å, $\alpha = 90°$ |
| | b = 9.0525(3) Å, $\beta = 98.612(3)°$ |
| | c = 12.9702(5) Å, $\gamma = 90°$ |
| Volume | 876.25(6) Å$^3$ |
| Z | 4 |
| Density (calculated) | 1.580 Mg/m$^3$ |
| Absorption coefficient | 1.893 mm$^{-1}$ |
| F(000) | 440 |
| Crystal size | 0.10 × 0.01 × 0.01 mm$^3$ |
| Theta range for data collection | 5.98 to 66.64° |
| Index ranges | −8 <= h <= 7, −10 <= k <= 10, −10 <= l <= 15 |
| Reflections collected | 5746 |
| Independent reflections | 1501 [R(int) = 0.0279] |
| Completeness to theta = 66.64° | 97.2% |
| Absorption correction | Semi-empirical from equivalents |
| Max. and min. transmission | 0.7528 and 0.6842 |
| Refinement method | Full-matrix least-squares on F$^2$ |
| Data/restraints/parameters | 1501/0/150 |
| Goodness-of-fit on F$^2$ | 1.056 |
| Final R indices [I > 2sigma(I)] | R1 = 0.0269, wR2 = 0.0696 |
| R indices (all data) | R1 = 0.0303, wR2 = 0.0718 |
| Largest diff. peak and hole | 0.215 and −0.224 e · Å$^{-3}$ |

The unit cell dimensions are defined by three parameters: length of the sides of the cell; relative angles of the sides to each other and the volume of the cell. The lengths of the sides of the unit cell are defined by a, b and c. The relative angles of the cell sides are defined by $\alpha$, $\beta$ and $\gamma$.

Figure 2:
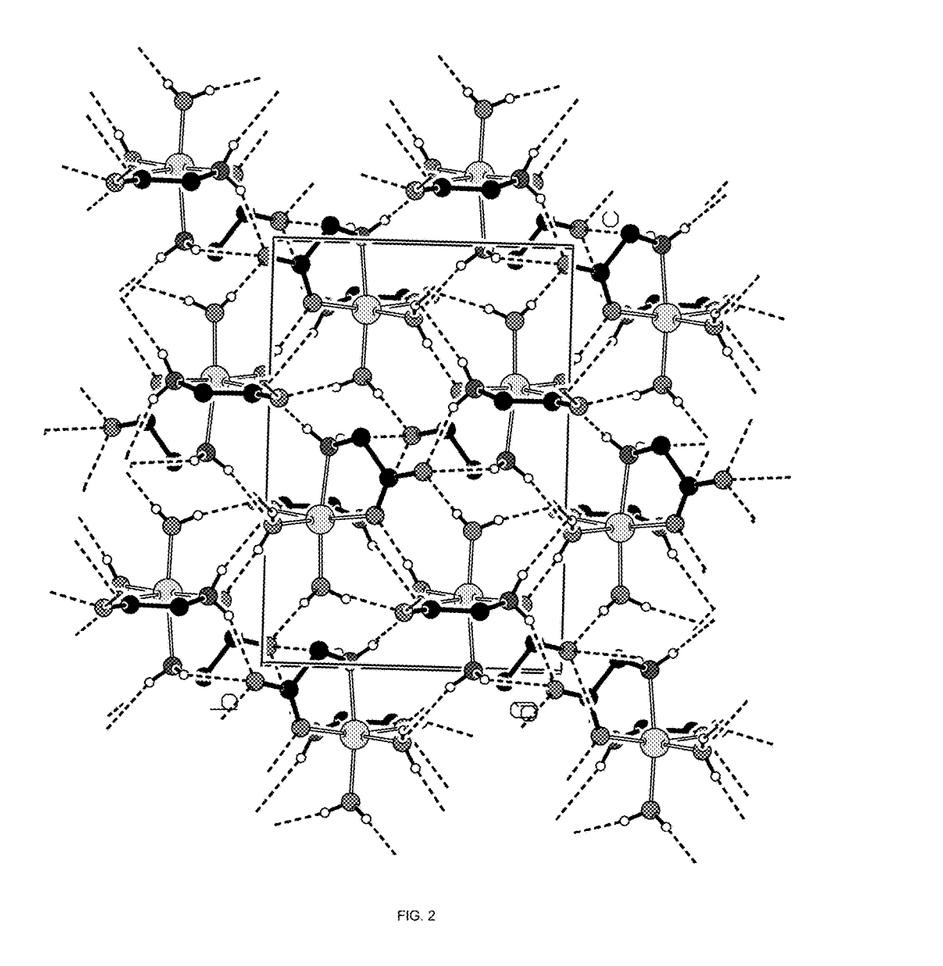
FIG. 2 depicts the crystal lattice structure of magnesium glycinate dihydrate.
Figure 3:
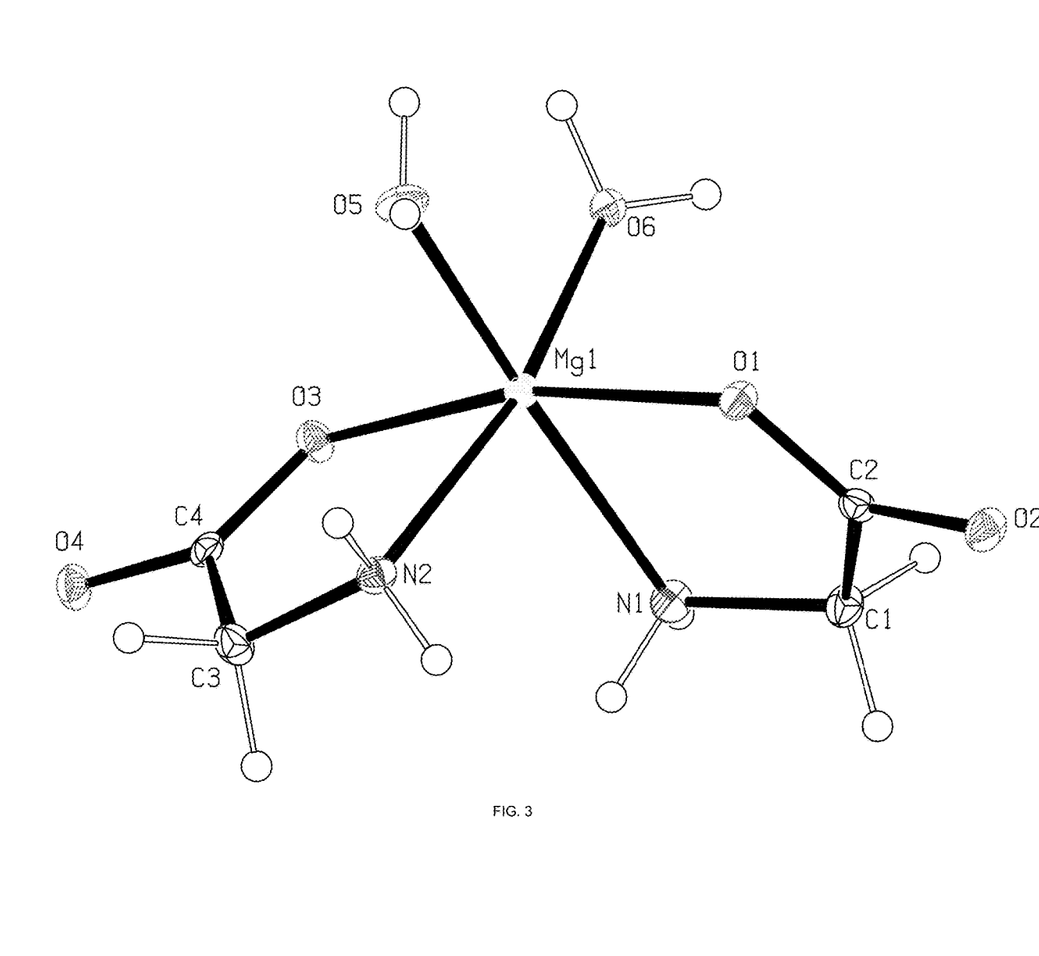
FIG. 3 depicts the solution structure of a single dihydrated complex of magnesium glycinate. It shows two water molecules coordinated as the di-hydrate.

Embodiments of the invention further include crystalline magnesium glycinate dihydrate having atomic positions of all the atoms relative to the origin of the unit cell as recited in Tables 3-6 and represented in FIG. 3. Tables 3 through 6 list the parameters of atomic coordinates and their isotropic displacement parameters, bond lengths and angles, anisotropic displacement parameters and hydrogen (proton) atom coordinates of crystalline magnesium glycinate dihydrate as described herein. These parameters define the absolute atomic arrangement in the crystal structure of magnesium glycinate dihydrate depicted in FIGS. 2 and 3.

TABLE 3

Atomic coordinates (×10$^4$) and equivalent isotropic displacement parameters (Å$^2$ × 10$^3$) for d12119. U(eq) is defined as one third of the trace of the orthogonalized U$^{ij}$ tensor.

| | x | y | z | U(eq) |
|---|---|---|---|---|
| Mg (1) | 4955(1) | 3183(1) | 1604(1) | 12(1) |
| O (1) | 6599(1) | 1363(1) | 1488(1) | 16(1) |
| O (2) | 7777(2) | −198(1) | 443(1) | 20(1) |
| O (3) | 3002(1) | 4804(1) | 1397(1) | 16(1) |
| O (4) | 85(1) | 5319(1) | 1178(1) | 19(1) |
| O (5) | 5111(2) | 3108(1) | 3184(1) | 20(1) |
| O (6) | 6936(2) | 4761(1) | 1775(1) | 16(1) |
| N (1) | 4885(2) | 2953(2) | −109(1) | 17(1) |
| N (2) | 2478(2) | 1838(1) | 1541(1) | 16(1) |
| C (1) | 6247(2) | 1896(2) | −337(1) | 17(1) |
| C (2) | 6920(2) | 936(2) | 601(1) | 14(1) |
| C (3) | 910(2) | 2796(2) | 1257(1) | 18(1) |
| C (4) | 1384(2) | 4431(2) | 1281(1) | 14(1) |

TABLE 4

Bond lengths [Å] and angles [°] for Magnesium Glycinate Dihydrate Polymorph

| | |
|---|---|
| Mg(1)—O(5) | 2.0365 (12) |
| Mg(1)—O(6) | 2.0566 (12) |
| Mg(1)—O(3) | 2.0685 (11) |
| Mg(1)—O(1) | 2.0817 (11) |
| Mg(1)—N(2) | 2.2224 (14) |
| Mg(1)—N(1) | 2.2249 (14) |
| O(1)—C(2) | 1.2702 (18) |
| O(2)—C(2) | 1.2464 (18) |
| O(3)—C(4) | 1.2548 (18) |
| O(4)—C(4) | 1.2591 (18) |
| O(5)—H(1O) | 0.85 (3) |
| O(5)—H(2O) | 0.83 (3) |
| O(6)—H(3O) | 0.83 (3) |
| O(6)—H(4O) | 0.87 (3) |
| N(1)—C(1) | 1.466 (2) |
| N(1)—H(1N) | 0.86 (2) |
| N(1)—H(2N) | 0.92 (2) |
| N(2)—C(3) | 1.469 (2) |
| N(2)—H(3N) | 0.86 (2) |
| N(2)—H(4N) | 0.90 (2) |
| C(1)—C(2) | 1.519 (2) |
| C(1)—H(1A) | 0.9900 |
| C(1)—H(1B) | 0.9900 |
| C(3)—C(4) | 1.522 (2) |
| C(3)—H(3A) | 0.9900 |
| C(3)—H(3B) | 0.9900 |
| O(5)—Mg(1)—O(6) | 89.02 (5) |
| O(5)—Mg(1)—O(3) | 94.99 (5) |
| O(6)—Mg(1)—O(3) | 90.77 (5) |
| O(5)—Mg(1)—O(1) | 95.83 (5) |
| O(6)—Mg(1)—O(1) | 97.23 (5) |
| O(3)—Mg(1)—O(1) | 166.63 (5) |
| O(5)—Mg(1)—N(2) | 86.58 (5) |
| O(6)—Mg(1)—N(2) | 168.22 (5) |
| O(3)—Mg(1)—N(2) | 78.74 (5) |
| O(1)—Mg(1)—N(2) | 94.09 (5) |
| O(5)—Mg(1)—N(1) | 172.49 (5) |
| O(6)—Mg(1)—N(1) | 94.64 (5) |
| O(3)—Mg(1)—N(1) | 91.52 (5) |
| O(1)—Mg(1)—N(1) | 77.22 (5) |
| N(2)—Mg(1)—N(1) | 91.05 (5) |
| C(2)—O(1)—Mg(1) | 120.19 (9) |
| C(4)—O(3)—Mg(1) | 119.13 (9) |
| Mg(1)—O(5)—H(1O) | 116.3 (14) |
| Mg(1)—O(5)—H(2O) | 122.5 (17) |
| H(1O)—O(5)—H(2O) | 111 (2) |
| Mg(1)—O(6)—H(3O) | 127.8 (15) |
| Mg(1)—O(6)—H(4O) | 120.5 (15) |
| H(3O)—O(6)—H(4O) | 105 (2) |
| C(1)—N(1)—Mg(1) | 110.45 (9) |
| C(1)—N(1)—H(1N) | 108.1 (14) |
| Mg(1)—N(1)—H(1N) | 121.8 (14) |
| C(1)—N(1)—H(2N) | 109.8 (14) |

TABLE 4-continued

Bond lengths [Å] and angles [°] for Magnesium Glycinate Dihydrate Polymorph

| | |
|---|---|
| Mg(1)—N(1)—H(2N) | 102.1 (13) |
| H(1N)—N(1)—H(2N) | 104 (2) |
| C(3)—N(2)—Mg(1) | 109.09 (9) |
| C(3)—N(2)—H(3N) | 107.8 (13) |
| Mg(1)—N(2)—H(3N) | 113.1 (13) |
| C(3)—N(2)—H(4N) | 110.7 (13) |
| Mg(1)—N(2)—H(4N) | 109.8 (13) |
| H(3N)—N(2)—H(4N) | 106.3 (18) |
| N(1)—C(1)—C(2) | 111.88 (12) |
| N(1)—C(1)—H(1A) | 109.2 |
| C(2)—C(1)—H(1A) | 109.2 |
| N(1)—C(1)—H(1B) | 109.2 |
| C(2)—C(1)—H(1B) | 109.2 |
| H(1A)—C(1)—H(1B) | 107.9 |
| O(2)—C(2)—O(1) | 124.97 (13) |
| O(2)—C(2)—C(1) | 117.32 (13) |
| O(1)—C(2)—C(1) | 117.69 (13) |
| N(2)—C(3)—C(4) | 113.06 (12) |
| N(2)—C(3)—H(3A) | 109.0 |
| C(4)—C(3)—H(3A) | 109.0 |
| N(2)—C(3)—H(3B) | 109.0 |
| C(4)—C(3)—H(3B) | 109.0 |
| H(3A)—C(3)—H(3B) | 107.8 |
| O(3)—C(4)—O(4) | 124.72 (14) |
| O(3)—C(4)—C(3) | 119.04 (13) |
| O(4)—C(4)—C(3) | 116.24 (13) |

TABLE 5

Anisotropic displacement parameters ($Å^2 \times 10^3$) for Magnesium Glycinate Dihydrate Polymorph. The anisotropic displacement factor exponent takes the form: $-2p^2[h^2 a^{*2} U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| Mg(1) | 13(1) | 11(1) | 13(1) | 0(1) | 1(1) | 1(1) |
| O(1) | 18(1) | 15(1) | 13(1) | 0(1) | 2(1) | 4(1) |
| O(2) | 24(1) | 18(1) | 18(1) | -2(1) | 1(1) | 9(1) |
| O(3) | 13(1) | 13(1) | 23(1) | 0(1) | 3(1) | -1(1) |
| O(4) | 15(1) | 17(1) | 25(1) | -2(1) | 5(1) | 4(1) |
| O(5) | 29(1) | 16(1) | 15(1) | 0(1) | 1(1) | -7(1) |
| O(6) | 14(1) | 19(1) | 17(1) | -3(1) | 4(1) | -2(1) |
| N(1) | 21(1) | 15(1) | 16(1) | 3(1) | 2(1) | 4(1) |
| N(2) | 18(1) | 13(1) | 16(1) | -1(1) | 2(1) | 0(1) |
| C(1) | 19(1) | 19(1) | 14(1) | 2(1) | 4(1) | 4(1) |
| C(2) | 12(1) | 14(1) | 16(1) | -1(1) | 1(1) | -2(1) |
| C(3) | 14(1) | 15(1) | 26(1) | -2(1) | 3(1) | -1(1) |
| C(4) | 16(1) | 16(1) | 10(1) | -2(1) | 4(1) | 1(1) |

TABLE 6

Hydrogen (proton) coordinates ($\times 10^4$) and isotropic displacement parameters ($Å^2 \times 10^3$) for Magnesium Glycinate Dihydrate Polymorph.

| | x | y | z | U(eq) |
|---|---|---|---|---|
| H(1A) | 7268 | 2442 | -551 | 21 |
| H(1B) | 5731 | 1257 | -926 | 21 |
| H(3A) | 44 | 2613 | 1745 | 22 |
| H(3B) | 319 | 2533 | 548 | 22 |
| H(1O) | 5010(30) | 2250(30) | 3452(17) | 40(6) |
| H(2O) | 5800(30) | 3640(30) | 3578(19) | 48(7) |
| H(3O) | 7850(30) | 4790(20) | 1495(16) | 35(6) |
| H(4O) | 7220(30) | 5230(30) | 2370(20) | 44(6) |
| H(1N) | 4920(30) | 3710(30) | -509(17) | 37(6) |
| H(2N) | 3750(30) | 2570(20) | -317(17) | 40(6) |

TABLE 6-continued

Hydrogen (proton) coordinates ($\times 10^4$) and isotropic displacement parameters ($Å^2 \times 10^3$) for Magnesium Glycinate Dihydrate Polymorph.

| | x | y | z | U(eq) |
|---|---|---|---|---|
| H(3N) | 2410(30) | 1140(20) | 1092(15) | 28(5) |
| H(4N) | 2450(30) | 1410(20) | 2164(16) | 32(5) |

General Methods of Providing Magnesium Glycinate Dihydrate:

Crystalline polymorphic magnesium glycinate (e.g., magnesium glycinate dihydrate of the polymorph form described herein) can be obtained by the following processes. Those of skill in the art will appreciate that the processes described below may be modified or adapted to produce different polymorphic forms (e.g., by changing solvents, combinations of solvents or temperature), monohydrates or multihydrates (e.g., by adjusting water content in a given solvent). Various solid forms of magnesium glycinate can be prepared by dissolving the compound in various suitable solvents and then causing the magnesium glycinate to return to the solid phase. Specific combinations of solvents and conditions under which magnesium glycinate returns to the solid phase are discussed in greater detail below. In a particular embodiment, magnesium glycinate dihydrate is obtained by heating magnesium methoxide and glycine under conditions described below.

A suitable solvent may solubilize magnesium glycinate and or its precursors (e.g., magnesium methoxide or glycine), either partially or completely. Examples of suitable solvents useful in the present invention are a protic solvent, a polar aprotic solvent, or mixtures thereof. In certain embodiments, suitable solvents include an ether, an ester, an alcohol, a ketone, or a mixture thereof. In certain embodiments, the suitable solvent is methanol, ethanol, isopropanol, or acetone wherein said solvent is anhydrous or in combination with water, methyl tert-butyl ether (MTBE) or heptane. In other embodiments, suitable solvents include tetrahydrofuran, 1,4-dioxane, dimethylformamide, dimethylsulfoxide, glyme, diglyme, methyl ethyl ketone, N-methyl-2-pyrrolidone, methyl t-butyl ether, t-butanol, n-butanol, and acetonitrile. In another embodiment, the suitable solvent is anhydrous ethanol. In some embodiments, the suitable solvent is MTBE.

According to another embodiment, the present invention provides a method for preparing a solid form of crystalline magnesium glycinate, comprising the steps of dissolving magnesium glycinate with a suitable solvent and optionally heating to form a solution thereof; and isolating crystalline hydrated magnesium glycinate.

As described generally herein, magnesium glycinate and/or its precursors may be dissolved in a suitable solvent, optionally with heating. In certain embodiments, magnesium glycinate or its precursors are dissolved at about 50 to about 60° C. In other embodiments, magnesium glycinate or its precursors are dissolved at about 50 to about 55° C. In still other embodiments, magnesium glycinate or its precursors are dissolved at the boiling temperature of the solvent. In other embodiments, magnesium glycinate or its precursors are dissolved without heating (e.g., at ambient temperature, approximately 20-25° C.).

In certain embodiments, magnesium glycinate precipitates from the mixture. In another embodiment, magnesium glycinate crystallizes from the mixture. In other embodiments, magnesium glycinate crystallizes from solution following seeding of the solution (i.e., adding crystals of magnesium glycinate to the solution).

Crystalline magnesium glycinate can precipitate out of the reaction mixture, or be generated by removal of part or all of the solvent through methods such as evaporation, distillation, filtration (e.g., nanofiltration, ultrafiltration), reverse osmosis, absorption and reaction, by adding an anti-solvent (e.g., water, MTBE and/or heptane), by cooling (e.g., crash cooling) or by different combinations of these methods.

As described generally above, crystalline magnesium glycinate is optionally isolated. It will be appreciated that magnesium glycinate may be isolated by any suitable physical means known to one of ordinary skill in the art. In certain embodiments, precipitated solid magnesium glycinate is separated from the supernatant by filtration. In other embodiments, precipitated solid magnesium glycinate is separated from the supernatant by decanting the supernatant. In some embodiments, crystalline magnesium glycinate is separated by evaporation of a solvent or supernatant.

In certain embodiments, precipitated solid magnesium glycinate is separated from the supernatant by filtration.

In certain embodiments, isolated crystalline magnesium dihydrate is dried in air. In other embodiments isolated crystalline magnesium dihydrate is dried under reduced pressure, optionally at elevated temperature.

In some embodiments of the invention, solid forms of magnesium glycinate are obtained through a production process capable of producing a form with a specified crystal morphology and that is substantially free of impurities such as magnesium hydroxide. In some embodiments, the production process results in magnesium glycinate dihydrate that is substantially free of solid impurities. The term "substantially free of solid impurities", as used herein, indicates that the amount of solid impurities is less than 10%, less than 9%, less than 8%, less than 7%, less than 6%, less than 5%, less than 4%, less than 3%, less than 2% or less than 1% by weight. In a particular embodiment, magnesium glycinate in the form of a dihydrated polymorph is obtained by adding an appropriate amount of glycine to a solution of magnesium methoxide and methanol, heating the solution, adding an appropriate volume of water to the solution and cooling the solution to crystallize out magnesium glycinate dihydrate. The reaction scheme is diagrammed below.

Magnesium Glycinate Dihydrate Process

In some embodiments, the magnesium glycinate dihydrate is the polymorphic form described by the XRPD data above and in FIGS. 1-3.

In some embodiments, a process for the preparation of crystalline magnesium glycinate dihydrate substantially free of impurities comprises about 20 kg+4 kg of magnesium methoxide (6-10% in methanol solution). In some embodiments, a process for the preparation of crystalline magnesium glycinate dihydrate substantially free of impurities comprises about 250 kg±50 kg of methanol (from 8% solution). In some embodiments, a process for the preparation of crystalline magnesium glycinate dihydrate substantially free of impurities comprises about 35 kg±7 kg of glycine. In some embodiments, a process for the preparation of crystalline magnesium glycinate dihydrate substantially free of impurities comprises about 140 kg±28 kg of deionized water.

In some embodiments, a process for the preparation of crystalline magnesium glycinate dihydrate substantially free of impurities comprises a water/magnesium methoxide (6-10% in methanol solution) ratio (v/v) of about 8:1, about 7:1, about 6.5:1 or about 6:1, or a range between any two of the numbers. In some embodiments, a process for the preparation of crystalline magnesium glycinate dihydrate substantially free of impurities comprises a water/magnesium methoxide (6-10% in methanol solution) ratio (v/v) of about 8:1-5:1. In some embodiments, a process for the preparation of crystalline magnesium glycinate dihydrate substantially free of impurities comprises a water/glycine weight ratio of about 5:1-3:1. In some embodiments, a process for the preparation of crystalline magnesium glycinate dihydrate substantially free of impurities comprises a methanol (8% solution)/water ratio (v/v) of about 3:1-1:1. In some embodiments, a process for the preparation of crystalline magnesium glycinate dihydrate substantially free of impurities comprises a methanol (8% solution)/magnesium methoxide ratio (v/w) of about 20:1-10:1.

Figure 4:
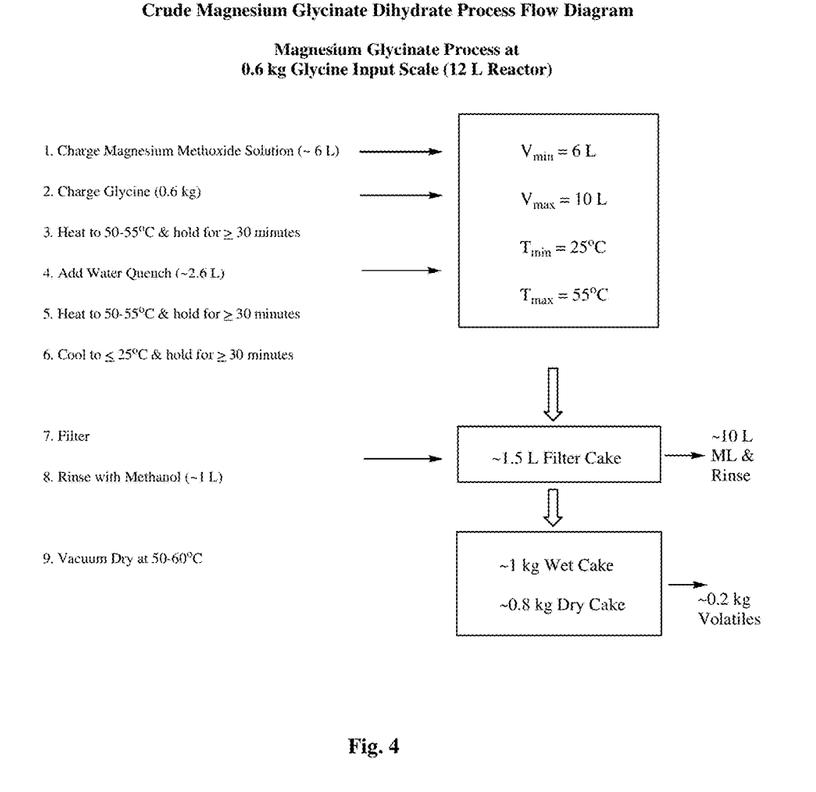
FIG. 4 is a flow diagram of a manufacturing process that may be used to produce solid forms of the invention.

In particular embodiments of the process, as exemplified in FIG. 4, magnesium methoxide is dissolved in an alcohol such that the magnesium methoxide is present in an amount of 6-10% in methanol solution. Glycine is then added to the magnesium methoxide solution. In some embodiments, the amount (weight) of glycine added in kilograms is about $\frac{1}{10}^{th}$ of the volume (L) of the solution. In other embodiments, the amount of glycine added in kilograms is about $\frac{1}{9}^{th}$, $\frac{1}{8}^{th}$, $\frac{1}{7}^{th}$ or more of the volume (L) of the solution. The mixture of magnesium methoxide solution and glycine is then heated to about 50-55° C. for approximately 30 minutes or more. After heating, water is added to quench the reaction, and the mixture is heated again to 50-55° C. for approximately 30 minutes or more. The mixture is cooled or allowed to cool to approximately 25° C. or less for at least 30 minutes, allowing crystalline magnesium glycinate dihydrate to precipitate from the solution. Magnesium glycinate dihydrate is then filtered from the solution, rinsed with methanol and vacuum dried at a temperature of approximately 50-60° C., thereby producing crystalline magnesium glycinate dihydrate of the forms described herein. Suitable alcohols include those having from 1 to about 12 carbon atoms, including, for example, methanol, ethanol, isopropyl alcohol, n-butyl alcohol, t-butyl alcohol and the like and mixtures thereof. Preferred solvents include methanol and ethanol, and most preferably methanol.

Those of skill in the art will appreciate that the amount of water in the reaction mixture determines the type of hydrate that is formed. The amount of water may be adjusted to form a monohydrate, dihydrate, trihydrate etc.

Uses, Formulation and Administration
Pharmaceutically Acceptable Compositions

According to another embodiment, the invention provides a composition comprising the crystalline polymorphs of magnesium dihydrate described herein and a pharmaceutically acceptable carrier, adjuvant, or vehicle. The amount of crystalline magnesium glycinate (e.g., magnesium glycinate dihydrate) in compositions of this invention may be such that it is effective to treat hyperphosphatemia in a subject. In certain embodiments, a composition of this invention is formulated for administration to a patient in need of such composition. In some embodiments, a composition of this invention is formulated for oral administration to a patient. In certain embodiments of the invention, the formulation for oral administration comprises an enteric coating. In some embodiments, the enteric coating contains acetyltributyl citrate, carbomers, cellulose acetate phthalate, cellulose acetate succinate, ethyl cellulose, guar gum, hypromellose acetate succinate, hypromellose phthalate, polymethacrylates, polyvinyl acetate phthalate, shellac, tributyl citrate, triethyl citrate, white wax and/or zein.

As described in the '012 application, it has been discovered that magnesium salts such as magnesium glycinate may interact differently with stomach acid which contains an overwhelming amount of HCl. Magnesium glycinate may react with stomach acid (HCl) to form magnesium chloride, which does not have the ability to bind phosphate in appreciable quantities. Thus, magnesium glycinate may lose its ability to precipitate phosphate in SIF and treat hyperphosphatemia. Therefore, it is desirable to enteric coat magnesium salts, in particular magnesium glycinate, such that magnesium salts are protected from stomach acids.

The term "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, Vitamin E polyethylene glycol succinate (d-alpha tocopheryl polyethylene glycol 1000 succinate), sodium carboxymethylcellulose, polyacrylates, waxes, polyethylene-polyoxypropylene-block polymers, and wool fat.

Compositions of the invention can be formulated for administration by injection, topically, orally, transdermally, or rectally. In some embodiments, a composition of the present invention is formulated for oral administration. Sterile injectable forms of the compositions of this invention may be an aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous and non-aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is typically combined with emulsifying and suspending agents. If desired, certain sweetening, flavouring, coloring or nutritional agents (e.g., vitamins, minerals, fatty acids or amino acids) may also be added.

Capsule dosages may contain magnesium glycinate dihydrate substantially in the form of a polymorph described herein within a capsule, which may be coated with gelatin. As mentioned, tablet and powder forms may comprise an enteric coating. Enteric coatings may comprise phthalic acid cellulose acetate, hydroxypropylmethyl cellulose phthalate, polyvinyl alcohol phthalate, carboxy methyl ethyl cellulose, a copolymer of styrene and maleic acid, a copolymer of methacrylic acid and methyl methacrylate, and like materials, and if desired, they may be employed with suitable plasticizers and/or extending agents. A coated capsule may have a coating on the surface of the capsule or may be a capsule comprising a powder or granules with an enteric-coating.

As used herein, the term "enteric coating" or "enteric film" refers to a barrier applied to, for example, oral medication that controls the location in the digestive system where the medication is absorbed. Typically, enteric coatings prevent release of medication before it reaches the small intestine. In some embodiments, enteric coatings suitable for the present invention include surface coatings that are stable at the highly acidic pH (e.g., pH~3) found in the stomach, but dissolve quickly at a less acidic (relatively more basic) pH (e.g., (above pH 5.5). According to the present invention, an enteric film or coating prevents dispersion of magnesium glycinate polymorphs in the acidic environment of the lumen of the stomach.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, joints, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of Compound 1 include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments of the invention, a polymorph of magnesium glycinate dihydrate as described herein is a component of a pharmaceutical composition that also comprises one or more additional therapeutic agents. In certain embodiments, the additional therapeutic agents are intended for the treatment of hyperphosphatemia. In particular embodiments, the additional therapeutic agents are selected from a group consisting of aluminium-containing phosphate binders, calcium-containing phosphate binders (e.g., calcium acetate), magnesium salts, phosphate-binding polymers (e.g. sevelamer hydrochloride (Bleyer, A. J. et al., *Am. J. Kidney Dis.*, 1999, 33:694-701)), and lanthanum carbonate (see, e.g., Joy, M. S. et al., *Am. J. Kidney Dis.*, 2003, 42:96-107). Additional magnesium salts that may be included in pharmaceutical compositions of the invention include magnesium arginate, magnesium betainate, magnesium hydroxide, magnesium lysinate and magnesium oxide.

In some embodiments, a composition of the invention can be a food, a drink, or a nutritional, food or dietary supplement. In one embodiment, the composition is a nutritional supplement. As used herein, "a nutritional supplement" is a preparation formulated to supply nutrients (including, but not limited to, vitamins, minerals, fatty acids or amino acids) that are missing or not consumed in sufficient quantity in a person's or animal's diet. As used in this application, a nutritional supplement is also referred to as "a food supplement" or "a dietary supplement."

Uses of Compounds and Pharmaceutically Acceptable Compositions

Phosphate-binding magnesium glycinate forms described herein can be used to bind and/or remove phosphate from a mammalian subject. In particular, phosphate-binding magnesium polymorphs described herein can be used to treat hyperphosphatemia. As used herein, the term "hyperphosphatemia" refers to a higher than normal blood level of phosphorous. In human adults, the normal range for blood phosphorous is approximately 2.5-4.5 mg/dL (i.e., 2.5-4.5 mg/100 mL). Typically, an individual with hyperphosphatemia condition has fasting serum phosphorus concentration higher than 5.0 mg/dL (e.g., higher than 5.5 mg/dL, 6.0 mg/dL, 6.5 mg/dL, or 7.0 mg/dL). Methods for measuring phosphate concentrations are well known in the art. For example, phosphate concentrations can be measured by the method of Lowry and Lopez, *J. Biol. Chem.* 162: 421-428. The hyperphosphatemia condition, especially if present over extended periods of time, leads to severe abnormalities in calcium and phosphorus metabolism and can be manifested by aberrant calcification in joints, lungs, and eyes.

Hyperphosphatemia is associated with various diseases or medical conditions including, but not limited to, diseases associated with inadequate renal function such as, for example, chronic kidney disease and/or end-stage renal disease, hypoparathyroidism, and other disorders of phosphate metabolism and/or impaired phosphate transport function.

In embodiments of the invention, a method of treating hyperphosphatemia includes administering to a subject in need of treatment a therapeutically effective amount of a crystalline form of magnesium glycinate. In some embodiments, the form is a dihydrated polymorph of magnesium glycinate, such as the one described in Tables 1-6. In some embodiments, a method of treating hyperphosphatemia includes administering to a subject in need of treatment a therapeutically effective amount of at least one magnesium glycinate dihydrate polymorph. As used herein, the term "therapeutically effective amount" refers to an amount effective to reduce or control serum phosphate level or to treat, prevent, and/or delay the onset of the symptom(s) caused by hyperphosphatemia when administered in a single dose or in a series of doses separated by appropriate time intervals, such as hours or days, to a subject suffering from or susceptible to a disease, disorder, and/or condition associated with hyperphosphatemia. A therapeutically effective amount is commonly administered in a dosing regimen that may comprise multiple unit doses. An appropriate unit dose within an effective dosing regimen is referred to as "therapeutically effective dose."

As used herein, an "individual," "patient" or "subject" being treated includes a human or a non-human such as, a non-human mammalian subject including, but not limited to, a bovine, cat, dog, ferret, gerbil, goat, guinea pig, hamster, horse, mouse, nonhuman primate, pig, rabbit, rat, or sheep. As used herein, a "subject susceptible to" a disease, disorder and/or condition associated with hyperphosphatemia refers to an individual at risk of developing hyperphosphatemia or to a patient reporting one or more of the physiological symptoms of hyperphosphatemia, even though a diagnosis of hyperphosphatemia may not have been made.

As used herein, the term "reduce," "decrease," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same condition of hyperphosphatemia as the individual being treated.

As used herein, the term "treat," "treatment," or "treating" refers to any method used to partially or completely alleviate, ameliorate, relieve, inhibit, prevent, delay onset of, reduce severity of and/or reduce incidence of one or more symptoms or features of hyperphosphatemia or of a particular disease, disorder, and/or condition underlying hyperphosphatemia. Treatment may be administered to a subject who does not exhibit signs of a disease and/or exhibits only early signs of the disease for the purpose of decreasing the risk of developing pathology associated with the disease. For prophylactic benefit, a composition of the invention may be administered to a patient at risk of developing hyperphosphatemia or to a patient reporting one or more of the physiological symptoms of hyperphosphatemia, even though a diagnosis of hyperphosphatemia may not have been made.

The actual amount effective for a particular application will depend on the condition being treated (e.g., the disease or disorder and its severity, and the age and weight of the patient to be treated) and the route of administration. Determination of an effective amount is well within the capabilities of those skilled in the art, especially in light of the disclosure herein. For example, the effective amount for use in humans can be determined from animal models. For example, a dose for humans can be formulated to achieve circulating and/or gastrointestinal concentrations that have been found to be effective in animals.

As described above, solid forms of crystalline magnesium glycinate encompassed by the present invention may be administered using any amount and any route of administration effective for treating or lessening the severity of hyperphosphatemia. The exact amount required will vary from subject to subject, depending on the species, age, and general condition of the subject, the severity of the infection, the particular agent, its mode of administration, and the like. Crystalline magnesium glycinate polymorphs (e.g., magnesium glycinate dihydrate) is preferably formulated in substantially morphological pure dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

In some embodiments of invention, the unit dosage forms are substantially morphologically pure, meaning that they are comprised substantially of only one crystal polymorph. For example, a unit dosage may be comprised of at least 75%, at least 80%, at least 85%, at least 90%, at least 95%, at least 98%, at least 99% or more a single polymorph described herein. In some embodiments of the invention, a unit dose may comprise at least 98% of the polymorphic form of magnesium glycinate dihydrate described in FIGS. 1-3 and Tables 1-6.

Successful treatment of hyperphosphatemia may be achieved by administration of the pharmaceutical compositions described above. In some embodiments, a therapeutically effective dose of a magnesium glycinate polymorph according to the invention may contain about 20 mg to 1200 mg of magnesium (e.g., about 20 mg to about 1000 mg of magnesium, about 20 mg to about 800 mg of magnesium, about 20 mg to about 600 mg of magnesium, about 20 mg to about 400 mg of magnesium, about 20 mg to about 200 mg of magnesium, about 100 mg to about 300 mg of magnesium, about 100 mg to about 500 mg of magnesium, about 100 mg to about 700 mg of magnesium, about 100 mg to about 900 mg of magnesium). In some embodiments, a therapeutically effective dose of a magnesium glycinate polymorph contains less than about 1200 mg of magnesium (e.g., less than about 1000 mg of magnesium, less than about 800 mg magnesium, less than about 600 mg of magnesium, less than about 400 mg of magnesium, or less than about 200 mg magnesium).

In some embodiments, compositions according to the invention, when administered according to a suitable dosing regimen, provide a therapeutically effective amount of magnesium glycinate polymorph ranging from about 60 mg to about 4000 mg (e.g., from about 80 mg to about 3000, from about 1000 mg to about 2000 mg, from about 500 mg to about 1200 mg, from about 500 mg to about 1100 mg, from about 500 mg to about 1000 mg) per day. In some embodiments, compositions according to the invention, when administered according to a suitable dosing regimen, provide more than about 500 mg (e.g., more than about 750 mg, more than about 1000 mg, more than about 1250 mg, more than about 1500 mg, more than about 1750 mg, or more than about 2000 mg) magnesium glycinate polymorph per day. In some embodiments, compositions according to the invention, when administered according to a suitable dosing regimen, provide less than about 4000 mg (e.g., less than about 3500 mg, less than about 3000 mg, less than about 2500 mg, less than about 2000 mg, less than about 1500 mg, or less than about 1000 mg) magnesium glycinate polymorph per day.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

The polymorphs described herein may be administered in combination with one or more additional therapeutic agents such as those described above. The additional agents may be administered separately from a magnesium glycinate-containing composition, as part of a multiple dosage regimen. Alternatively, those agents may be part of a single dosage form, mixed together with a magnesium glycinate polymorph in a single composition. If administered as part of a multiple dosage regime, the two active agents may be submitted simultaneously, sequentially or within a period of time from one another (e.g., one hour, two hours, six hours, twelve hours, one day, one week, two weeks, one month).

As used herein, the terms "combination," "combined," and related terms refer to the simultaneous or sequential administration of therapeutic agents in accordance with this invention. For example, a magnesium glycinate polymorph may be administered with another therapeutic agent simultaneously or sequentially in separate unit dosage forms or together in a single unit dosage form. Accordingly, the present invention provides a single unit dosage form comprising a magnesium glycinate polymorph (e.g., the magnesium glycinate dihydrate as described in FIG. 1-3 and Table 1-6), an additional therapeutic agent, and a pharmaceutically acceptable carrier, adjuvant, or vehicle.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1: Preparation of Crystalline Magnesium Glycinate Dihydrate

A polymorph of magnesium glycinate dihydrate was prepared by the process described in FIG. 4. Magnesium methoxide (6-10% in methanol solution), methanol, glycine and nitrogen gas were obtained. Raw material calculations were conducted as follows:

Using a vacuum, the target amount of magnesium methoxide (in methanol solution) was transferred into a primary 200-gallon reactor. The net active amount of magnesium methoxide in the solution was determined by multiplying the net solution weight by the solution assay and then dividing the result by 100. The target amount of magnesium methoxide was the net active magnesium methoxide weight in the solution. Magnesium methoxide was the limiting reagent in the reaction.

The target amount of glycine was transferred into clean polyethylene (LDPE) bags. The magnesium methoxide solution in the 200-gallon reactor was stirred while the glycine was transferred into the reactor while nitrogen purge of the reactor head space was maintained. After all of the glycine had been added, the temperature of the reactor contents was heated to 50-55° C. with a maximum jacket temperature of 70° C. The reactor was maintained at this temperature for at least 30 minutes. Meanwhile, the net amount of methanol in the magnesium methoxide solution was determined by subtracting the net active weight of the magnesium methoxide from the total solution weight.

The target weight of deionized water for quenching was calculated by multiplying the total methanol weight by a factor of 0.568. The target weight of deionized water was then transferred to the primary reactor over a period of at least 5 minutes. The reactor contents were again heated to 50-55° C. with a maximum jacket temperature of 70° C., and maintained at said temperature for at least 30 minutes.

After at least 30 minutes, the reactor was cooled to approximately 15-25° C. and maintained at said temperature for at least 30 minutes. At the end of 30 minutes, abundant precipitate crystals were present in the solution.

The precipitated crystals were collected by a vacuum filter dryer. A magnesium glycinate dihydrate slurry was filtered on the filter drying using recirculated mother liquor as necessary to facilitate the transfer of the slurry. The solid was collected and lightly compressed into a filter cake.

The filter cake was de-liquored for at least 10 minutes by blowing nitrogen through the filter cake. A targeted amount of methanol rinse was then used to wash the magnesium glycinate. The methanol rinse was transferred to the filter dryer and the collected magnesium glycinate dihydrate washed by displacement washing. After the wash was complete, the collected magnesium glycinate dihydrate was de-liquored for at least 10 minutes by blowing nitrogen through the filter cake.

TABLE 7

Magnesium Glycinate Dihydrate Synthesis Stoichiometry and Batch Factor Calculation

| Material | MW | Density | Weight Kg | Volume Liters | Moles | Molar Equiv | Volumes | Batch factor |
|---|---|---|---|---|---|---|---|---|
| Magnesium methoxide Active Weight (6-10% solution) | 86.37 | | 22.00 | | 254.71 | 1.0 | | 1.000 |
| Methanol (From 8% Solution) | 32.04 | 0.792 | 253.0 | 319.4 | | | 14.5 | |
| Glycine | 75.07 | 1.61 | 38.243 | | 509.43 | 2.0 | | 1.7383 |
| Deionized Water | 18.01 | 1.00 | 143.7 | 143.7 | | | 6.5 | 0.568 × Methanol weight |
| Methanol Rinse | 32.04 | 0.792 | 50.43 | 63.8 | | | 2.89 | 2.2924 |

Wet magnesium glycinate dihydrate filter cake was then transferred to a vacuum shelf dryer (Stokes) and dried under at least 28 inches Hg of pressure at 50-60° C. for at least 12 hours. The weight of the filter cake was monitored during drying. Drying continued until the magnesium glycinate dihydrate reached a constant weight (less than or equal to 1% loss over 4 hours of drying).

Example 2: X-Ray Diffraction Experiments

Single Crystal X-Ray Analysis

A single crystal of the magnesium glycinate dihydrate (identification code d12119) was isolated from a powder sample prepared as above. The isolated crystal was analysed by X-ray crystallography. Data were collected on a Bruker Kappa APEX-DUO diffractometer using a Copper ImuS (microsource) tube with multi-layer optics and were measured using a combination of φ scans and ω scans. The data was processed using APEX2 and SAINT (Bruker, 2007, APEX2, SAINT & SADABS, Bruker AXS Inc., Madison, Wis., USA). Absorption corrections were carried out using SADABS (Bruker, 2007). The structure was solved and refined using SHELXTL (Sheldrick, G. M., *Acta. Cryst.*, 2008, A64: 112-122) for full-matrix least-squares refinement that was based on $F^2$. All H atoms bonded to C atoms were included in calculated positions and allowed to refine in riding-motion approximation with U~iso~ tied to the carrier atom. H atoms bonded to O and N atoms were refined independently with isotropic displacement parameters.

The following results were obtained:

TABLE 8

| | |
|---|---|
| Empirical formula | $C_4 H_{12} Mg N_2 O_6$ |
| Formula weight | 208.47 |
| Temperature | 147(2) K |
| Wavelength | 1.54178 Å |
| Crystal system | Monoclinic |
| Space group | P 21/n |
| Unit cell dimensions | a = 7.5481(3) Å, α = 90° |
| | b = 9.0525(3) Å, β = 98.612(3)° |
| | c = 12.9702(5) Å, γ = 90° |
| Volume | 876.25(6) Å$^3$ |
| Z | 4 |
| Density (calculated) | 1.580 Mg/m$^3$ |
| Absorption coefficient | 1.893 mm$^{-1}$ |
| F(000) | 440 |
| Crystal size | 0.10 × 0.01 × 0.01 mm$^3$ |
| Theta range for data collection | 5.98 to 66.64° |
| Index ranges | −8 <= h <= 7, −10 <= k <= 10, −10 <= l <= 15 |
| Reflections collected | 5746 |
| Independent reflections | 1501 [R(int) = 0.0279] |
| Completeness to theta = 66.64° | 97.2% |
| Absorption correction | Semi-empirical from equivalents |
| Max. and min. transmission | 0.7528 and 0.6842 |
| Refinement method | Full-matrix least-squares on $F^2$ |
| Data/restraints/parameters | 1501/0/150 |
| Goodness-of-fit on $F^2$ | 1.056 |
| Final R indices [I > 2sigma(I)] | R1 = 0.0269, wR2 = 0.0696 |
| R indices (all data) | R1 = 0.0303, wR2 = 0.0718 |
| Largest diff. peak and hole | 0.215 and −0.224 e · Å$^{-3}$ |

Crystal structures defined by these parameters are represented in FIGS. 2 and 3. These experiments confirmed that the process of Example 1 resulted in a single dihydrated polymorph of magnesium glycinate.

X-Ray Powder Diffraction Analysis

Two samples of magnesium glycinate dihydrate powder prepared as above were submitted for X-ray Powder Diffraction Analysis ("XRPD"). The analysed lot numbers were designated as 428-192 and 428-194. Powder samples were gently packed in standard sample holders. Excess powder was removed by a glass edge to achieve a flat surface and minimize the orientation of the crystallites in the packed powder.

Both samples were run on an automated Siemens/Brukker D5000 diffractomter. The system was equipped with a high power line focus Cu-kα source operating at 50 kV/35 mA. A solid-state Si/Li Kevex detector was used for removal of k-beta lines. The diffractometer and the detector were periodically calibrated with provided Quartz ceramic plate for zero-correction.

The diffraction patterns were collected on a theta/2-theta Bragg-Brentano reflection geometry with fixed slits as follow: divergence slit 1.0 mm., scattering slit 1.0 mm and receiving slit of 0.2 mm. A step scan mode was used for data acquisition with step size of 0.02° 2-theta and counting time of 1.5 s. per step. Data processing was carried out with Bruker AXS software Eva™ v.8.0.

XRPD analysis (FIG. 1) showed the material to be crystalline and capable of being unambiguously characterized by at least one characteristic peak identified by 2-theta values as follows:

TABLE 9

| No. | 2-Theta ° | Δ 2θ (±)° | d, Å |
|---|---|---|---|
| 1 | 14.6 | 0.1 | 6.06 |
| 2 | 16.0 | 0.1 | 5.54 |
| 3 | 16.9 | 0.1 | 5.25 |
| 4 | 17.6 | 0.1 | 5.04 |
| 5 | 19.3 | 0.1 | 4.59 |
| 6 | 22.9 | 0.1 | 3.88 |
| 7 | 24.4 | 0.1 | 3.65 |
| 8 | 25.8 | 0.1 | 3.45 |
| 9 | 30.9 | 0.1 | 2.89 |
| 10 | 47.1 | 0.1 | 1.93 |

The results of a single crystal X-ray analysis are limited to one crystal placed in a X-ray beam XRPD provides crystallographic data on a large group of crystals. If the powder is a pure crystalline compound, a simple powder diagram is obtained. To compare the results of a single crystal analysis and powder X-ray analysis, the single crystal data can be computationally converted into a powder X-ray diagram. An XRPD pattern can be calculated from single crystal X-ray diffraction because the single crystal experiment routinely determines the unit cell dimensions, space group, and atomic positions. By comparing this calculated powder pattern and the powder pattern experimentally obtained from a large collection of crystals, it is possible to confirm if the results of the two techniques are the same; i.e., if the crystals in the XRPD samples match the structure of the single crystal.

This experiments was conducted on two powders samples (designated DL-428-194 and DL-428-192), which were compared to a calculated XRPD pattern from the single-crystal analysis above. The results are shown in FIG. 1. The upper two plots corresponds to the experimentally derived XRPD pattern for their respective samples, and the second plot corresponds to the XRPD calculated from the single crystal X-ray data.

The peak overlap indicated that the two techniques yield the same results. The primary powder X-ray diffraction peaks provided an unambiguous description of a polymorph of magnesium glycinate dihydrate produced by the process of Example 1. Identical patterns from two separate samples indicated that the process routinely produces the same polymorph. The near perfect similarity between the primary X-ray powder diffraction peaks of the samples and the peaks calculated from the crystal structure indicated that the process of Example 1 resulted in a morphological pure single polymorph matching the crystal structure described in Tables 2-6. The lattice parameters for the bulk material differed slightly from the ones obtained from the single crystal structure solution. This is common in the field and was due to the fact that the single crystal experiment was carried out at low temperature (−120° C.), while the x-ray powder diffraction data was collected at room temperature. At low temperature most of the molecular structures tend to shrink their lattices.

Example 3—Phosphate Binding Assays

Exemplary stock solutions suitable for phosphate-binding assays include the following: phosphate-binding solution ("PBS") containing 10 mM $KH_2PO_4$, 30 mM $Na_2CO_3$, 80 mM NaCl, as described in Rosenbaum et al. *Nephrol. Dial. Transplant.* 12:961-964 (1997); acetate buffer ("AB") solution containing 0.1N acetic acid, 0.025N sodium acetate, as described in Lowry & Lopez *J. Biol. Chem.* 162:421-428 (1946); ammonium molybdate ("AM") solution containing 1% ammonium molybdate in 0.05N $H_2SO_4$, as described in Lowry & Lopez; ascorbic acid ("AA") solution containing 1% ascorbic acid in $H_2O$, as described in Lowry & Lopez.

In general, the phosphate-binding assays are conducted in 12×75 mm glass tubes. 4.0 mL PBS and 20 mg putative phosphate binder are added to a glass tube and then mixed for 1 h at room temperature. 0.1 mL supernatant is pipetted from this tube to a new test tube. 3.0 mL AB, 0.3 mL AA and 0.3 mL AM solutions are added and O.D. is measured at 700 nm after 10 minutes. The assay is linear over the range used in this example.

The phosphate binding capacity was calculated as follows (mcg stands for micrograms):

$((O.D.\ of\ sample \times 95)/O.D.\ of\ standard) \times 40 = (mcg)\ PO_4$ left in solution $((3800\ (mcg)PO_4\ left) \times 50)/1000 = (mcg)PO_4$ bound per gram of phosphate binder.

The phosphate binding capacities of samples of magnesium glycinate dihydrate produced by the process of Example 1 are measured. X-ray powder diffraction is conducted on each of the samples to verify that they consist of the polymorph described in Example 2. Hypothetical results are presented below:

TABLE 10

Exemplary phosphate-binding results

| Sample | $PO_4$ binding, mg/g |
|---|---|
| 1 | 175.0 |
| 2 | 177.0 |
| 3 | 176.2 |
| 4 | 178.1 |

Considering a degree of experimental error inherent in the phosphate binding assays, each sample of the polymorph possesses a substantially equivalent phosphate binding capacity, suggesting that the phosphate-binding capacity of a magnesium glycinate salt is related to the process by which the salt is produced and the type of crystals produced by the process.

Example 4: Preparation of an Oral Formulation with an Enteric Coating

An oral formulation that contains the magnesium glycinate dihydrate polymorph of Example 2 is prepared as follows. The magnesium glycinate dihydrate polymorph of the examples above, one excipient suitable for enteric coating, one or more pharmaceutically acceptable excipients, and other appropriate ingredients (e.g., a lubricant) are mixed until a degree of uniformity suitable for pharmaceutical formulation is reached. The mixture is shaped into tablets or caplets. Tablets or caplets are then coated with at least one excipient suitable for enteric coating.

Example 5: Treatment of Hyperphosphatemia

An oral formulation containing the magnesium glycinate dihydrate polymorph prepared as described in the examples above is used to treat human patients suffering from hyperphosphatemia. Therapeutic formulations may be prepared to comprise a unit dose of 300 mg magnesium glycinate. One patient who has not taken a phosphate-binder may have a serum phosphorus level between about 5.5 and about 7.5 mg/dL. Two units of the formulation are orally administered to the patient three times daily with meals. A second patient has a serum phosphorus level between about 7.5 and about 9.0 mg/dL and has not taken a phosphate binder. Three units of the same formulation are orally administered to the patient three times daily with meals. The third patient has a serum phosphorus level greater than about 9.0 mg/dL and has not taken a phosphate binder. Four units of the formulation are orally administered to the patient three times daily with meals.

In each case, a patient's serum phosphorus level may be reduced to and remain in the range from 3.5 to 5.5 mg/dL after treatment according to the dosing regimen described above. A dosing regimen can be maintained relatively unchanged when the serum phosphorus level is within the range of 3.5 to 5.5 mg/dL.

INCORPORATION OF REFERENCES

All publications and patent documents cited in this application are incorporated by reference in their entirety to the same extent as if the contents of each individual publication or patent document were incorporated herein.

What is claimed is:

1. A process of manufacturing magnesium glycinate dihydrate comprising:
   dissolving magnesium methoxide and glycine in methanol to provide a first solution;
   heating the first solution at approximately 50-55° C. for at least 30 minutes;
   adding water to the first solution to provide a second solution;
   heating the second solution at approximately 50-55° C. for at least 30 minutes; and
   cooling the second solution to approximately 25° C. or less.

2. The process of claim 1, wherein magnesium glycinate dihydrate precipitates from the second solution.

3. The process of claim 1, wherein magnesium glycinate dihydrate crystallizes from the second solution.

4. The process of claim 3, further comprising isolating crystalline magnesium glycinate.

5. The process of claim 1, wherein crystalline magnesium glycinate dihydrate is generated by removal of solvent from the second solution.

* * * * *